(12) United States Patent
Nicolson et al.

(10) Patent No.: US 11,405,592 B2
(45) Date of Patent: Aug. 2, 2022

(54) SYSTEM AND METHOD FOR SELECTING COLONIES

(71) Applicant: Becton, Dickinson and Company, Franklin Lakes, NJ (US)

(72) Inventors: Strett Roger Nicolson, Owings Mills, MD (US); Mark Sakowski, Cockeysville, MD (US); Paul Fieni, Sparks, MD (US); Mark Larsen, Sparks, MD (US); Keri Lynne Jones Aman, Lutherville, MD (US); Amy Alcott Llanso, Henderson, NV (US); Harry Yuheng Chou, Cockeysville, MD (US)

(73) Assignee: BECTON, DICKINSON AND COMPANY, Franklin Lakes, NJ (US)

( * ) Notice: Subject to any disclaimer, the term of this patent is extended or adjusted under 35 U.S.C. 154(b) by 226 days.

(21) Appl. No.: 16/347,007

(22) PCT Filed: Nov. 2, 2017

(86) PCT No.: PCT/US2017/059745
§ 371 (c)(1),
(2) Date: May 11, 2018

(87) PCT Pub. No.: WO2018/085559
PCT Pub. Date: May 11, 2018

(65) Prior Publication Data
US 2019/0270959 A1 Sep. 5, 2019

Related U.S. Application Data

(60) Provisional application No. 62/417,942, filed on Nov. 4, 2016.

(51) Int. Cl.
G06K 9/00 (2022.01)
H04N 7/18 (2006.01)
(Continued)

(52) U.S. Cl.
CPC ............ H04N 7/183 (2013.01); C12M 33/04 (2013.01); C12M 41/14 (2013.01); C12M 41/48 (2013.01); G06V 10/235 (2022.01); G06V 20/69 (2022.01)

(58) Field of Classification Search
None
See application file for complete search history.

(56) References Cited

U.S. PATENT DOCUMENTS

2012/0275681 A1* 11/2012 Honda ................. C12M 33/02
                                                    382/133
2014/0219538 A1* 8/2014 Guthrie ................ G06K 9/469
                                                    382/133
2014/0349131 A1 11/2014 Seki

FOREIGN PATENT DOCUMENTS

EP     2497823 A1    9/2012
JP     2012073197 A  4/2012
(Continued)

OTHER PUBLICATIONS

Choudhry ("High-Throughput Method for Automated Colony and Cell Counting by Digital Image Analysis Based on Edge Detection", PLOS One, Feb. 5, 2016, pp. 1-23). (Year: 2016).*

(Continued)

Primary Examiner — Wei Wen Yang
(74) Attorney, Agent, or Firm — Knobbe, Martens, Olson & Bear LLP

(57) ABSTRACT

Systems and methods are provided for selecting colony locations. Selecting colony locations can include determine a location of a selection tool on a culture plate image, determining a location of a potential source of error on the culture plate image, comparing the location of the selection tool to the location of the potential source of error; and (Continued)

determining an error when the location of the selection tool overlays the location of the potential source of error.

27 Claims, 11 Drawing Sheets

(51) Int. Cl.
*C12M 1/26* (2006.01)
*C12M 1/00* (2006.01)
*C12M 1/36* (2006.01)
*G06V 10/22* (2022.01)
*G06V 20/69* (2022.01)

(56) References Cited

FOREIGN PATENT DOCUMENTS

| JP | 2012-080802 A | 7/2018 |
|---|---|---|
| WO | WO 2011/055791 A1 | 12/2011 |
| WO | WO 2013/147610 | 10/2013 |
| WO | WO 2016/191646 A2 | 12/2016 |

OTHER PUBLICATIONS

Copan Diagnostics, Inc. Redefining the Future of Automated Specimen Processing (May 13, 2016) [The date is according to the document properties.] [Retrieved from the Internet Mar. 21, 2018: <https://tools.thermofis her.com/content/sfs/brochures/COPAN-WASPLab-Product-Overview-EN .pdf>]; in entirety.

Faron, et al. Automated Scoring of Chromogenic Media for Detection of Methicillin-Resistant *Staphylococcus aureus* by Use of WASPLab Image Analysis Software. J Clin Microbiol. Mar. 2016, 54(3):620-624, Abstract; p. 621, col. 2.

International Search Report and Written Opinion dated May 10, 2018 for PCT/US2017/059745, filed Nov. 2, 2017.

Jones, Peter, et al. "Integration of image analysis and robotics into a fully automated colony picking and plate handling system." Nucleic acids research 20.17 (1992): 4599-4606.

Supplementary European Search Report dated May 11, 2020 in European Patent Application No. 17867515.3.

\* cited by examiner

SYSTEM AND METHOD FOR SELECTING COLONIES

RELATED U.S. APPLICATIONS

This application claims priority to U.S. Provisional Appl. No. 62/417,942 filed on Nov. 4, 2016, which is hereby incorporated by reference in its entirety.

BACKGROUND

Field

This invention relates to culture plate analysis, and more particularly to software for reviewing and analyzing culture plate images.

Description of the Related Art

Methods and systems for locating and selecting a colony of microorganisms are known. For example, methods for identifying microorganisms using mass spectrometry, in particular MALDI-TOF-MS (Matrix Assisted Laser Desorption and Ionization Time-of-Flight Mass Spectrometry) and the related systems for performing such methods are known. Such systems and methods are described, for example, in WO2013/147610 to Botma et al., the disclosure of which is incorporated by reference herein. Botma et al., teaches a method for locating and selecting a colony of microorganisms by obtaining an initial image of a culture dish, having a researcher or analyst manually select a colony of mircoorganisms in the initial image. The system then captures a second image of the culture dish from a position below a device for picking up a microorganism sample from the culture dish. The initial image and the second image are then compared to determine which colony was selected.

SUMMARY

Aspects of the invention include systems, devices, and methods for selecting colony locations on a culture plate image.

One embodiment is a system for selecting colony locations on a culture plate image. The system includes a computer system. The computer system includes a user interface configured to display a culture plate image and a selection tool and a processor. The processor is configured to determine a location of the selection tool on the culture plate image, determine a location of a potential source of error on the culture plate image, compare the location of the selection tool to the location of the potential source of error; and determine an error when the location of the selection tool overlays the location of the potential source of error.

Another embodiment is a method for selecting colony locations on a culture plate image. The method includes determining a location of a selection tool on the culture plate image, determining a location of a potential source of error on the culture plate image, comparing the location of the selection tool to the location of the potential source of error, and determining an error when the location of the selection tool overlays the location of the potential source of error.

DETAILED DESCRIPTION

Figure 1:
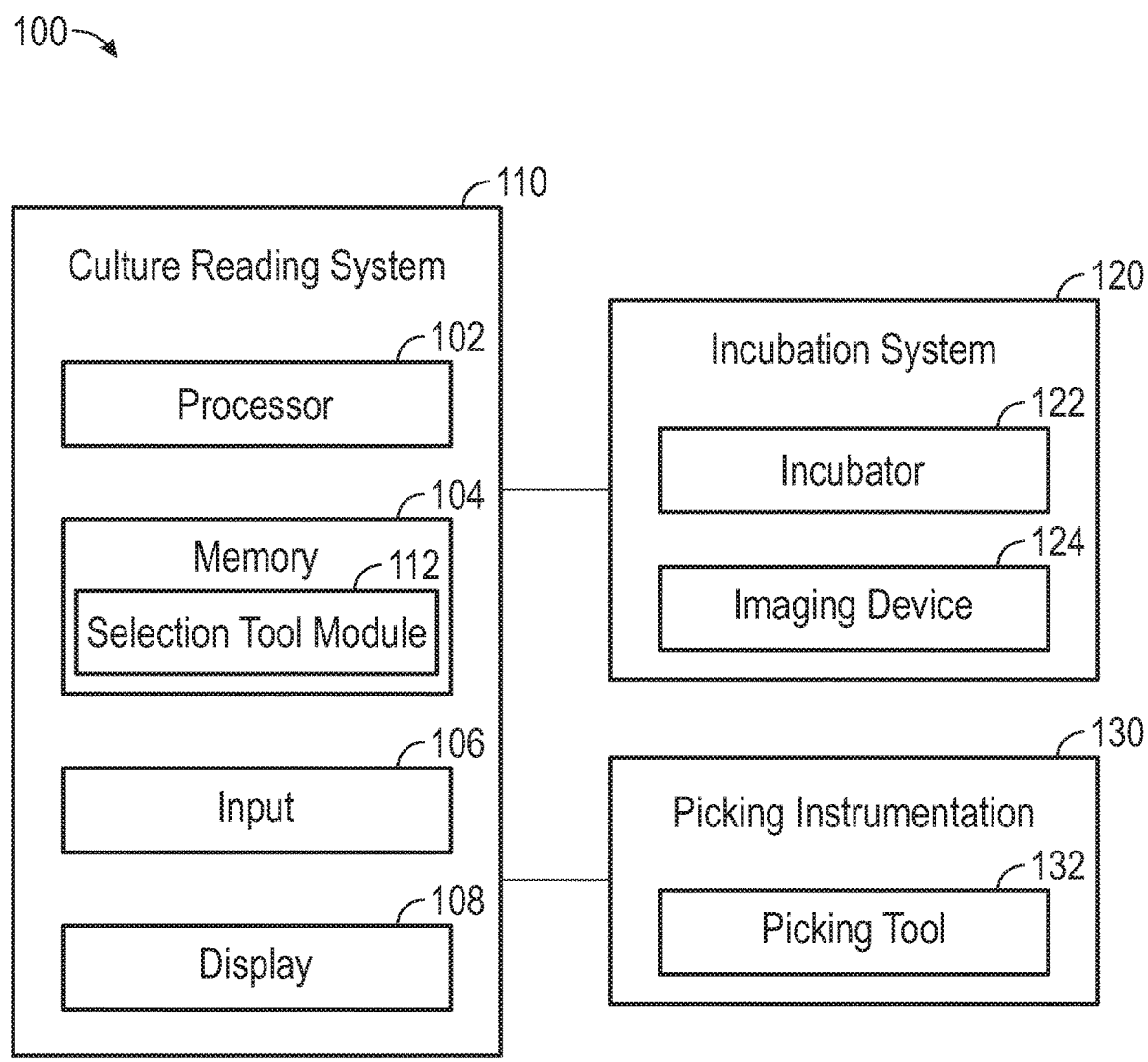
FIG. 1 depicts a schematic view of a colony selection system in accordance with an illustrative embodiment of the present invention.

As will be appreciated by one skilled in the art, there are numerous ways of carrying out the examples, improvements, and arrangements for colony selection in accordance with embodiments of the invention disclosed herein. Although reference will be made to the illustrative embodiments depicted in the drawings and the following description, these embodiments are not meant to be exhaustive of the various alternative designs and embodiments that are encompassed by the disclosed invention. Those skilled in the art will readily appreciate that various modifications may be made, and various combinations can be made, without departing from the invention.

Embodiments relate to systems and methods for selecting a colony or other feature from a culture plate. In one embodiment the culture plate is a petri dish and the system provides a variety of selection tools adapted to electronically select specific colonies for later processing. The selection tool may be a modified mouse cursor configured to allow for the selection of one or more colony locations on a culture plate image displayed on colony selection display screen of a culture reading system. In use, the system provides an interface that allows a user to conveniently select particular colony locations from one or more images taken of the culture plate. By providing back-end processing, the system can detect, and prevent, the user from selecting colony locations that don't meet predefined criteria. A selected colony location can be used by a user or instrumentation to perform a physical removal of a colony on the culture plate that corresponds to the selected colony location.

In one embodiment, the system determines if the colony location being selected is too close to an adjacent colony location that has already been selected. Thus, if a user attempts to select a colony location that is within a predetermined boundary of another selected colony location, the on-screen selection tool may indicate that such a selection is not available. In one embodiment the selection tool may change from a target indicator, to a red circle with a strike-through line to indicate that the chosen colony location is not available for selection. In another embodiment, the on-screen selection tool may change into other or different geographic indicia to indicate that the selection is not available. This process prevents the user from selecting a colony location that is too close to another colony location. A culture plate may include multiple organisms and adjacent colonies may represent different organisms. Restricting a user from selecting a colony location that is too close to another colony location can prevent removal of an undesired organism or a mixing of organisms when the adjacent colony locations correspond to different organisms. In some embodiments, the system also detects if the user is attempting to select colony locations that are adjacent other features of the culture plate, such as an edge, lip, or other protrusion from the culture plate. This features protects an electronic colony picker that is configured to contact the colony corresponding to the chosen colony location from striking or impinging on features of the culture plate.

FIG. 1 depicts a schematic view of an illustrative embodiment of a colony selection system 100. The colony selection system 100 includes a culture reading system 110, an incubation system 120, and picking instrumentation 130.

The incubation system 120 includes an incubator 122 and an imaging device 124. The incubator 122 can be configured to house and incubate one or more culture plates containing microorganisms and media for culturing the growth of the microorganisms. The imaging device 124 can be configured to capture and store images of the culture plates housed within the incubator 122. In some embodiments, the incubation system 120 is a ReadA Compact incubator.

The incubation system 120 can be configured to communicate with the culture reading system 110 via wired or wireless communication, cell communication, Bluetooth®, ZigBee®, LAN, WLAN, RF, IR, or any other communication method or system known in the art. For example, the incubation system 120 can be configured to transmit images of culture plates housed within the incubator 122 to the culture reading system 110.

In some embodiments, the incubation system 120 can be configured to transmit images of culture plates housed within the incubator 122 to an external database or image file storage system. The external database or image file storage system can be configured to transmit the images to the culture reading system 110 for use.

The culture reading system 110 includes a processor 102, a memory 104, an input 106, and a display 108. The memory 104, which can include both read-only memory (ROM) and random access memory (RAM), can be configured to provide instructions and data to the processor 102. For example, the memory 104 can store one or more modules that store data values defining instructions to configure processor 102 to perform functions of the culture reading system 110. As shown in FIG. 1, the memory 104 includes a selection tool module 112 that includes instructions that configure the processor 102 to perform selection tool functions as described herein. The memory 104 can also be configured to store images of culture plates received from the incubation system 120.

The display 108 can be configured to display data from the memory 104 and data received from the input 106. The input 106 can include one or more devices that allow a user to input data into the culture reading system 110. For example, the input 106 can include a keyboard, a mouse, and/or a touch screen in connection with the display 108. The input 106 and display 108 can operate to form a user interface presented on the display 108. The user interface can include one or more interactive display screens which provide culture plate data to a user and allow for data selection and manipulation.

In an illustrative embodiment of the present invention, the culture reading system 110 can be configured to display one or more culture plate images on the user interface provided on the display 108. In some embodiments, the culture reading system 110 can be configured to display a plurality of culture plate images simultaneously. The culture plate images can be retrieved from the memory 104, received from the incubation system 120, and/or received from another external device. The culture reading system 110 can allow for selection and/or manipulation of one or more of the plate images via the user interface presented on the display 108. In an illustrative embodiment of the present invention, the culture reading system 110 can facilitate selection of one or more colony locations on a culture plate image, wherein each colony location represents the location of a colony of biological material on the culture plate to which the image corresponds based on instructions stored within the selection tool module 112. For example, the culture reading system 110 can be configured to display an interactive colony selection display screen on the display 108 in response to a colony selection initiation event, such as a command from a user via the input 106.

In some embodiments, the selection tool module 112 is configured to cause the culture reading system 110 to provide a selection tool within the colony selection display screen for the selection of colony locations. The selection tool can be a cursor configured to allow for the selection of one or more colonies locations on a culture plate image displayed on colony selection display screen of the culture reading system 110. The position of the selection tool on the colony selection display screen can be manipulated using the input 106.

In some embodiments, the culture reading system 110 can be configured to determine the location of the culture plate image on the colony selection display screen. For example, the culture reading system 110 can determine or assign geographical coordinates for the culture plate image. The culture reading system 110 can also be configured to determine the location of the selection tool. For example, the culture reading system 110 can determine the geographical coordinates of the selection tool as compared to the geographical coordinates of the culture plate image. In some embodiments, the selection tool is configured to become visible when a cursor for interacting with the user interface scrolls over the culture plate image. For example, the cursor may change in appearance to become the selection tool when positioned over the culture plate image.

In some embodiments, the selection tool can allow for the selection of colony locations on the culture plate image that correspond to colonies of interest on the culture plate to which the image corresponds, such as colonies desired for use in diagnostic testing. The culture reading system 110 can be configured to correlate a selected colony location with coordinates on the culture plate shown in the culture plate image at which a picking tool, such as a pipetting tool, can be applied to pick up the desired colony. For example, each selected colony location can be stored as coordinates from a known/fixed position on the culture plate. In some embodiments, each selected colony location is stored as coordinates from the center of the culture plate. In some embodiments, each selected colony location can also be stored with a number indicating the order in which the colony location was selected. In some embodiments, the order in which the colony locations were selected corresponds to the order for picking the desired colonies from the culture plate. In some embodiments, the selection tool module 112 is configured to cause the culture reading system 110 to mark a selected colony location on the culture plate image with a visual icon or graphical indicia. The visual icon and/or coordinates correlated with the selected colony location can provide guidance to a user or automated picking tool for picking up a desired colony from the culture plate.

In some embodiments, desired colonies can be picked from a culture plate by the picking instrumentation 130. Picking instrumentation 130 can include an automated platform that robotically controls a picking tool 132 to pick up, pipette, or otherwise remove a desired colony from a culture plate. The culture reading system 110 can be configured to transmit data representing the coordinates of the desired colonies based on the colony location selections made using the selection tool or an image of the culture plate including markings at the locations of the desired colonies. The culture reading system 110 can be configured to communicate with the picking instrumentation 130 via wired or wireless communication, cell communication, Bluetooth®, ZigBee®, LAN, WLAN, RF, IR, or any other communication method or system known in the art. The picking instrumentation 130 can be configured to use the picking tool on the culture plate at the coordinates received from the culture reading system 110 or at the position of the markings shown on the image of the culture plate provided by the culture reading system 110. In some embodiments, the picking instrumentation 130 can be configured to align a culture plate image received from the culture reading system in the same orientation as the culture plate in order to match the coordinates and/or markings of selected colonies on the culture plate image with the desired colonies on the culture plate prior to pipetting. For example, the picking instrumentation 130 can be configured to run software that compares the orientation of the culture plate with that of the culture plate image and aligns the culture plate image so that the selected colony markers are in alignment with the desired colonies on the culture plate.

In some embodiments, the selection tool on the colony selection display screen can be shaped and sized to account for the shape and size of the picking tool 132 and/or a mechanical tolerance of the picking tool 132. For example, an outer edge of the selection tool can be shaped and sized to indicate a range of positions on the culture plate at which the picking tool 132 may pick the culture if the picking instrumentation 130 is provided the coordinates represented by a colony location selected using the selection tool. In other words, the selection tool can be shaped and sized such that any of the contents shown on the culture plate image within the outer edge of the selection tool may be picked by the picking tool 132 if a colony location selection is made at the location of the selection tool.

Some locations on the colony selection display screen may be invalid for colony selection. In some embodiments, the culture reading system 110 can be configured to determine invalid colony selection locations based on instructions from the selection tool module 112. Invalid colony selection locations can include colony selection locations that may lead to failed or erroneous pipetting by the picking tool 132. For example, it may be undesirable to select a colony location in which the tolerance of the picking tool 132 can allow for the picking tool to strike an edge of the culture plate or a culture plate divider. It can also be undesirable to select a colony location for a culture plate that is in a proximity to a previously selected colony location of the culture plate that, based on the tolerance of the picking instrumentation 130, can allow for the same colony to be picked by the picking tool 132 as that of the previously selected colony location.

In an illustrative embodiment, the selection tool module 112 can be configured to cause the culture reading system 110 to determine the location of one or more culture plate features that can act as potential sources of error, such as a culture plate edge, a culture plate divider, a previously selected colony, for example, using image processing software. The memory 104 can store a table of possible errors relating to the features of the culture plate. In some embodiments, the culture reading system 110 can be configured to determine the geographical coordinates of the culture plate features that can act as potential sources of error. The selection tool module 112 can further be configured to cause the culture reading system 110 to compare the location of the potential sources of error with the location of the selection tool. For example, the culture reading system 110 can be configured to compare the geographical coordinates of the selection tool with the geographical coordinates of one or more of the culture plate features. The selection tool module 112 can also be configured to cause the culture reading system 110 to determine when the selection tool overlays a potential source of error. For example, the culture reading system 110 can be configured to determine when there is a risk that the picking tool 132 will strike the edge of the culture plate, for example, when the section of the culture plate image representing the edge of the culture plate is positioned within the interior of the outer edge of the selection tool. The culture reading system 110 can also be configured to determine when there is a risk that the picking tool 132 will pick the same colony for two colony location selections, for example, when a marker indicating the previous colony location selection is positioned within the interior of the outer edge of the selection tool. The culture reading system 110 can also be configured to determine when there is a risk that the picking tool 132 will be deployed at a position outside of the culture plate based on a comparison of the location of the selection tool and the location of the edge of the culture plate and/or the interior of the culture plate.

In some embodiments, the selection tool module 112 can be configured to cause the culture reading system 110 to determine coordinate locations of all potential colony location selections on the culture plate image, for example, using image processing software. The culture reading system 110 can determine coordinate locations for each location on the culture plate image that corresponds to a colony on the culture plate. The culture reading system 110 can also determine which locations on the culture plate image that correspond to a colony on the culture plate do not risk an invalid colony selection. In some embodiments, the culture reading system 110 can be configured to identify an organism to which a colony corresponds or a difference between colonies depicted on the culture plate image indicating that the colonies correspond to different organisms, e.g., different color or shape on differential media types, for example, using image processing software. In some embodiments, the culture reading system 110 can be configured to allow for a selection of colony locations corresponding to colonies of a particular organism. In some embodiments, the culture reading system 110 can be configured to prevent selection of a colony locations corresponding to one type of organism if the colony selection tool is currently configured to select locations of a different type. In some embodiments, the selection tool can be configured to allow for a selection of an isolate number indicating a colony corresponding to a particular organism and a marking of one or more colonies with the isolate number. The culture reading system can prevent selection of colony locations that correspond to colonies corresponding to a different particular organism unless a different isolate number is selected.

In some embodiments, the selection tool can be configured to change appearance to provide a visual indication as to whether a valid colony location selection can be performed at a current location of the selection tool. For example, the size, shape, and/or color of the selection tool can change based on the location of the selection tool in comparison to various contents shown on the culture plate image, such as the sources of error described herein. For example, the selection tool can be configured to change appearance to indicate that the selection tool is positioned within the interior of the culture plate within the culture plate image. The selection tool can also be configured to change appearance to indicate that the selection tool is positioned outside of the edges of the culture plate within the culture plate image. The selection tool can also be configured to change appearance to indicate that the selection tool is positioned over the edges of the culture plate or a divider within the culture plate as shown on the culture plate image. In some embodiments, the selection tool can change appearance to indicate that the selection tool is positioned over a previously selected colony.

In some embodiments, the selection tool module 112 can be configured to cause the culture reading system 110 to prohibit selection of a colony location if it is determined that the colony location may result in an error of the picking instrumentation 130. For example, the culture reading system 110 can be configured to prohibit selection of a colony location if it is determined that the colony location is outside of the edge of the culture plate, overlaps the edge of the culture plate or a divider within the culture plate, or overlaps a previously selected colony location.

Figure 2:
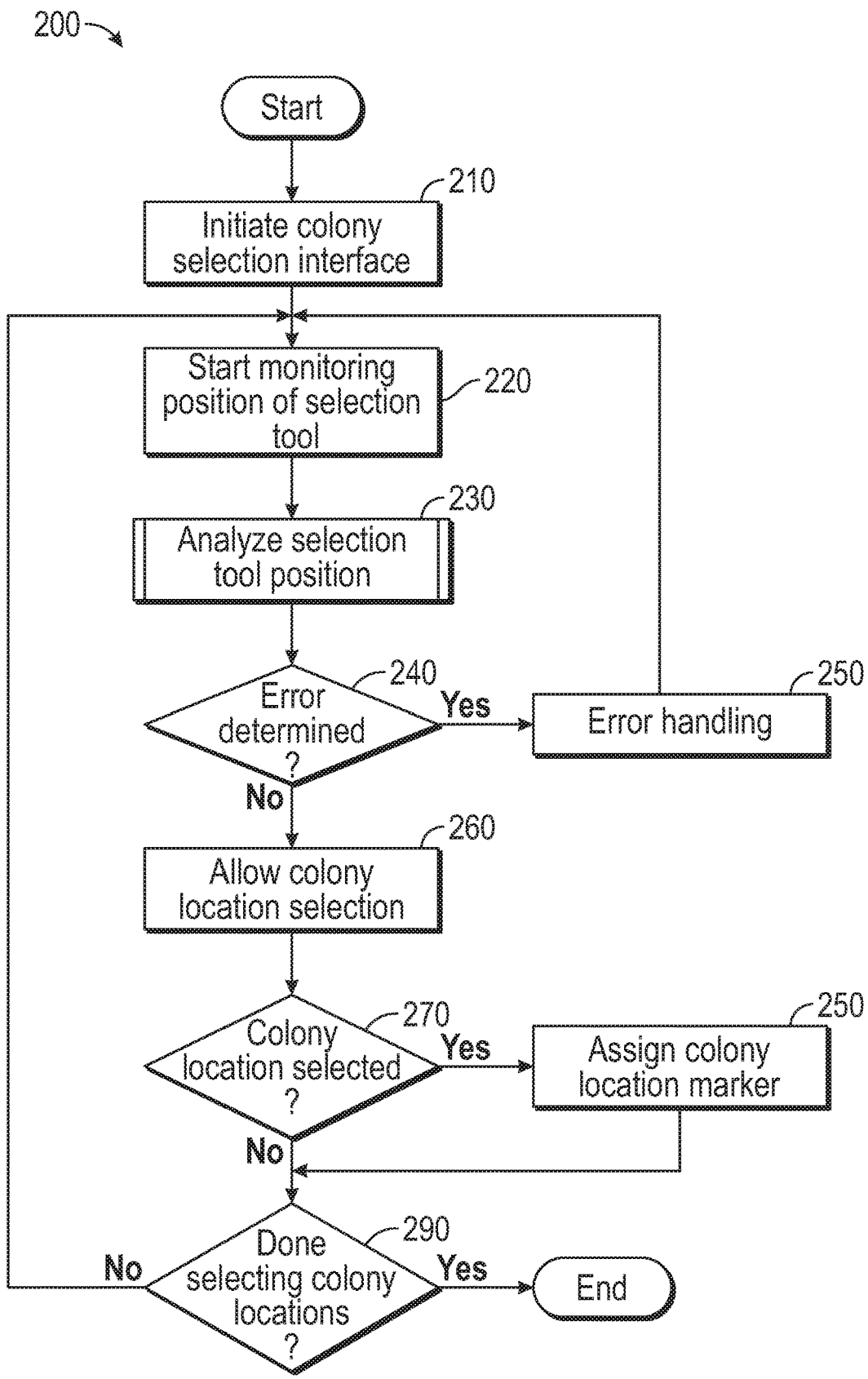
FIG. 2 depicts a flowchart of an embodiment of selecting colony locations in accordance with an illustrative embodiment of the present invention.

FIG. 2 depicts a flowchart of a process 200 of an illustrative embodiment of a method for selection of colony locations using a culture reading system such as culture reading system 110. The process 200 begins at a step 210, wherein a colony selection interface is initiated. A colony selection interface can include one or more display screens on a display, such as display 108, that allow for the selection of colony locations on an image of a culture plate. The colony selection interface can also include a selection tool for the selection of colony locations. As described above, the selection tool can be a cursor configured to move across the display and to allow for the selection of one or more colony locations on a culture plate image displayed on the colony selection interface. The colony selection interface may be part of a culture reading software application providing various options for analyzing and manipulating one or more culture plate images. The colony selection interface may be initiated by navigating to the colony selection interface through the culture reading software application.

After initiation of the colony selection interface, the process 200 moves to a step 220 wherein the position of the selection tool on the display starts to be monitored. The position of the selection tool can be monitored by a processor, such as processor 102, running a software application. The processor can monitor the position of the selection tool on the display or the position of the selection tool relative to a reference point on the culture plate image. The selection tool can be shaped and sized to overlay a desired colony depicted on the culture plate image. The selection tool can also be shaped and sized to account for the shape and size of a picking tool for pipetting a colony from the culture plate, such as picking tool 132, and/or a mechanical tolerance of a picking tool being operated by an automated pipetting system, such as picking instrumentation 130. Accordingly, the picking tool may extend over a range of coordinates on the culture plate image. The processor can monitor each coordinate overlaid by the selection tool at a given time. The processor can also monitor a center coordinate representing the center of the selection tool at a given time. In some embodiments, the processor can monitor the coordinates of an outer edge of the selection tool at a given time.

After the position of the selection tool starts to be monitored, the process 200 moves to a process step 230, wherein the position of the selection tool is analyzed. The position of the selection tool can be analyzed by a processor, such as processor 102, running a software application. In some embodiments, analysis of the position of the selection tool includes a comparison between the location of the selection tool and the location of one or more features of the culture plate shown on the culture plate image. For example, in some embodiments, analysis of the position of the selection tool includes a comparison of the position of the selection tool to the position of an edge of the culture plate, a divider of the culture plate, and/or a previously selected colony location on the culture plate image. The processor can be configured to determine that there is an error associated with the position of the selection tool if the position of the selection tool overlays a feature of the culture plate that is a potential source of error for picking a desired colony from the culture plate. For example, the processor can be configured to determine that there is an error associated with the selection tool if the position of the selection tool is outside of the edge of the culture plate or overlays one or more of the edge of the culture plate, a divider of the culture plate, and a previously selected colony location on the culture plate image. Such selection tool locations may represent locations at which a picking tool may not be able to pick the appropriate colony due to obstruction, by the edge of the culture plate or divider, for example, or due to a risk of pipetting a colony from a previously selected colony location. In some embodiments, each coordinate covered by the selection tool is compared to the location of the one or more features of the culture plate. In some embodiments, a center coordinate of the selection tool is compared to the location of the one or more features of the culture plate and it is determined whether any of the one or more features of the culture plate are within a predetermined distance of the center of the selection tool. The distance from the center of the selection tool can correspond to the outer edge of the selection tool as shown on the culture plate image.

After the position of the selection tool is analyzed, the process 200 moves to a decision step 240, wherein a decision is made whether an error has been determined at the position of the selection tool. If an error has been determined, the process 200 moves to a step 250, wherein error handling is performed. Error handling can include changing the appearance of the selection tool to indicate an error. For example, error handling can include changing the appearance of the selection tool to indicate that the selection tool is positioned outside of the edge of the culture plate, over the edge or divider of the culture plate, or over a previously selected colony location. In some embodiments, the shape, size, and or color of the selection tool can change to indicate an error. Error handling may also include preventing a selection of a colony location when an error is determined. After error handling, the process 200 returns to step 220.

If a decision is made at step 240 that an error did not occur, the process 200 moves to a step 260, wherein a selection of a colony location is allowed at the position of the selection tool. In some embodiments, when a colony location selection is allowed, a user can make a colony location selection using an input, such as input 106. In some embodiments, a colony location selection can be performed by a software application.

After selection of a colony location is allowed, the process 200 moves to a decision step 270, wherein a decision is made whether a colony location is selected. If a determination is made that a colony location is selected, the process 200 moves to a step 280, wherein a colony location marker is assigned to the selected colony. The colony location marker can include a colony location number to allow for tracking and distinguishing of particular colonies. In some embodiments, each colony location marker receives a number based on the order in which the colony location was selected. In some embodiments, the colony location marker can receive an isolate number indicating an organism corresponding to the colony corresponding to the colony location. Multiple colonies locations can be selected for the same organism. Consequently, multiple colony location markers can include the same isolate number. The colony location marker can also correspond to the shape and size of the selection tool. The colony location marker can correspond to the shape and size of the picking tool and/or a mechanical tolerance of an automated pipetting system. The shape and size of the marker can allow for a comparison between the position of the marker and the selection tool as described with respect to step 230 to determine if the position of the selection tool overlays the position of the marker.

After a colony marker is assigned at step 280 or if it is determined that a colony location is not selected at step 270, the process 200 moves to a decision step 290, wherein a decision is made if colony locations are finished being selected. It can be determined that colony locations are done being selected based on an input by a user. In some embodiments, it can be determined that colony locations are done being selected if a maximum number of colony locations have been selected. The maximum number of colony locations may be specific to the type of culture plate or to a planned diagnostic testing procedure for the organisms on the culture plate.

If the colony locations are not finished being selected, the process 200 returns to step 220. If the colony locations are done being selected, the process 200 concludes.

Figure 3:
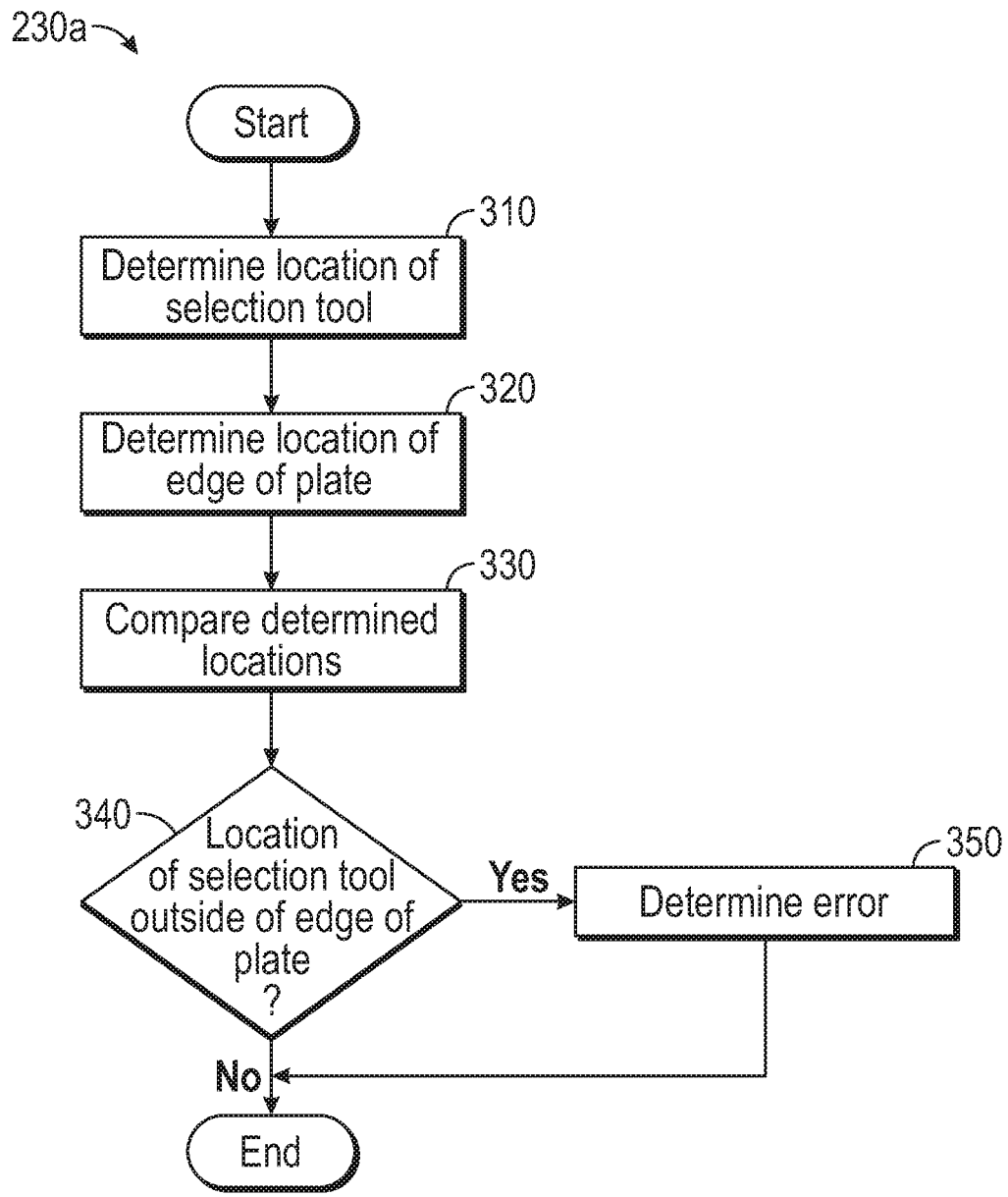
FIG. 3 depicts a flowchart of an embodiment of analyzing the position of a selection tool in accordance with an illustrative embodiment of the present invention.
Figure 4:
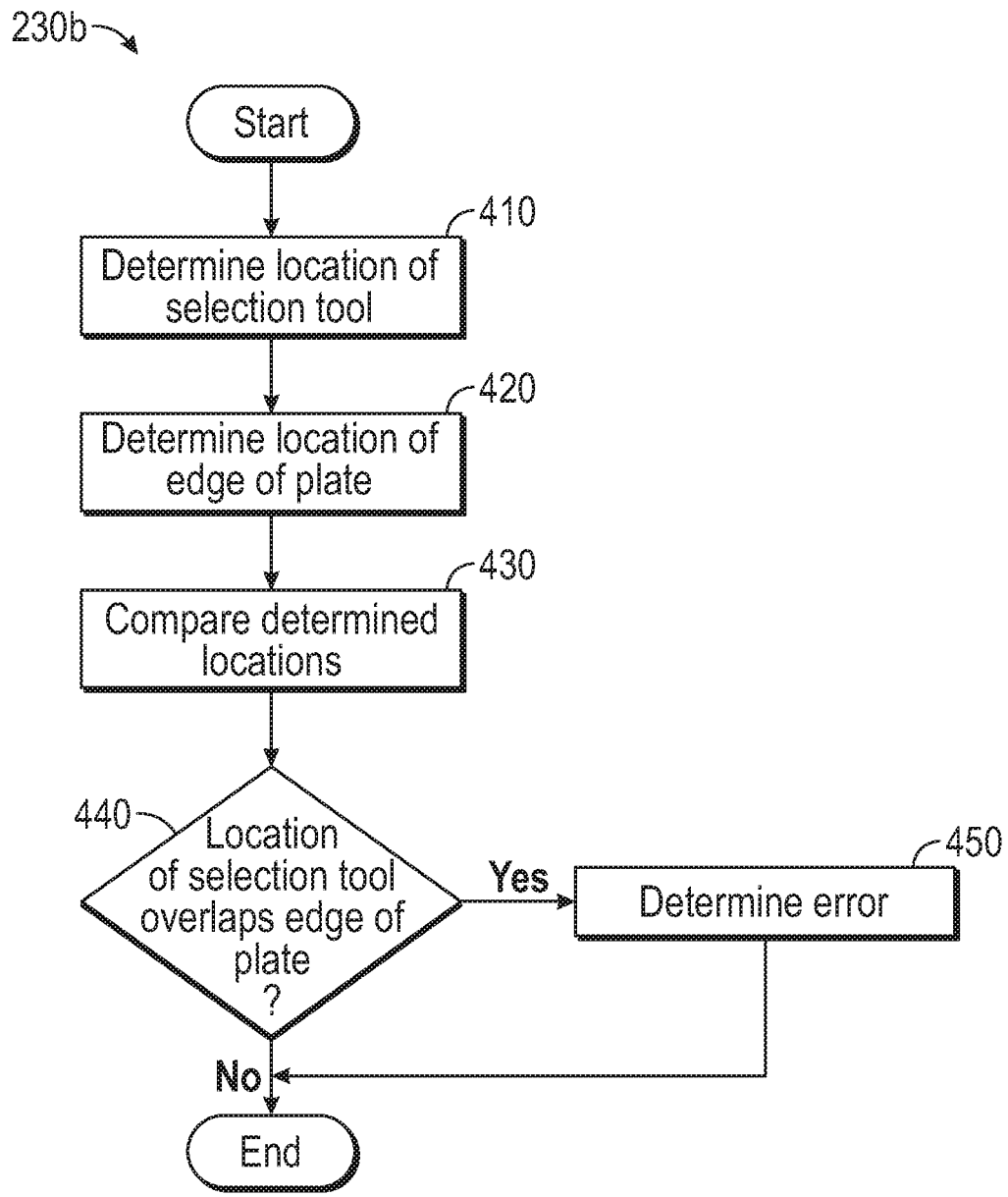
FIG. 4 depicts a flowchart of an embodiment of analyzing the position of a selection tool in accordance with an illustrative embodiment of the present invention.
Figure 5:
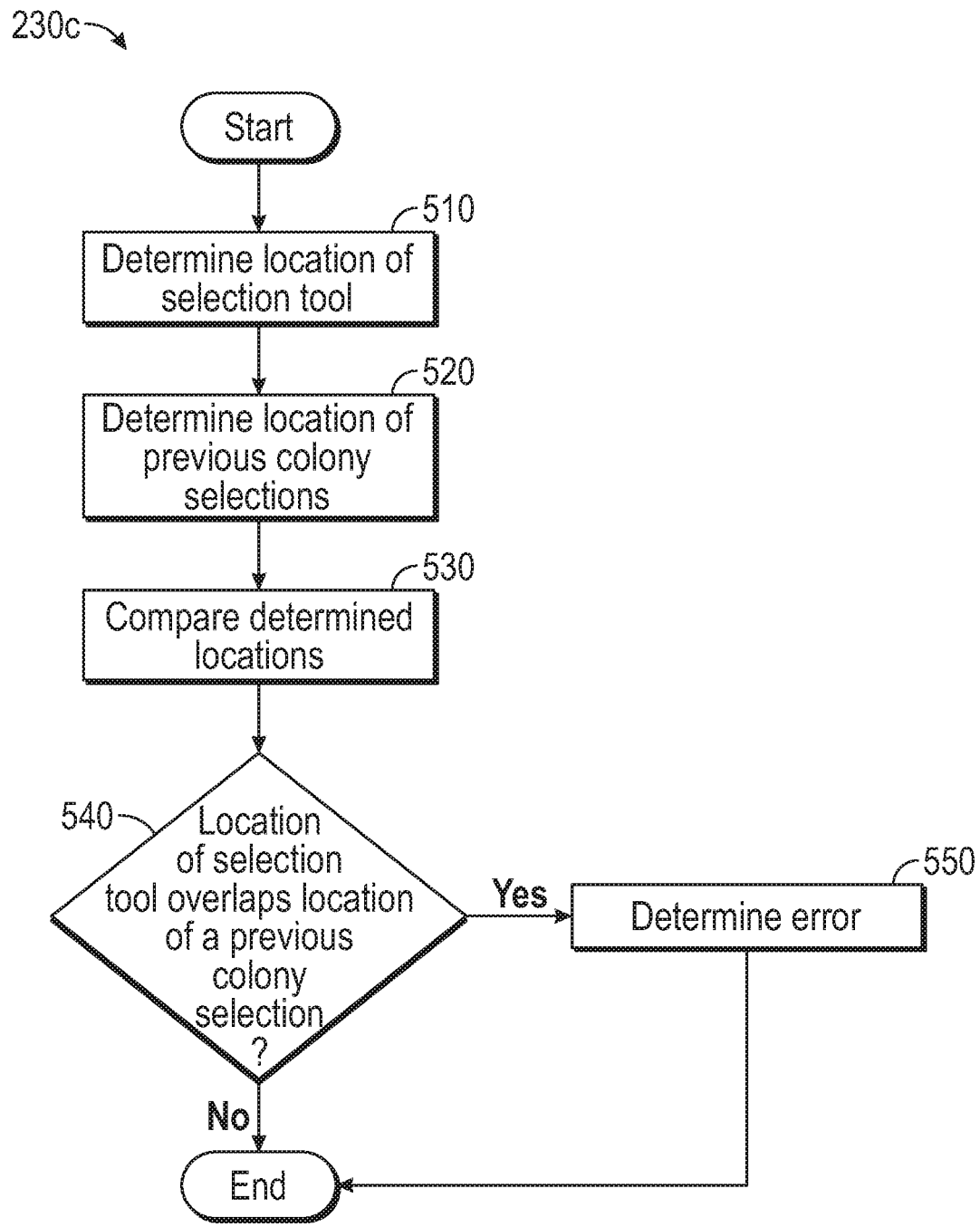
FIG. 5 depicts a flowchart of an embodiment of analyzing the position of a selection tool in accordance with an illustrative embodiment of the present invention.

FIGS. 3-5 each depict a flowchart of different illustrative embodiments of the process 230 for analyzing the position of the selection tool. For clarity, the embodiments of the process 230 shown in FIGS. 3-5 will be referred to as processes 230a, 230b, and 230c, respectively.

The process 230a provides an example of analyzing the position of the selection tool to determine if the selection tool is positioned outside of the peripheral edge of the culture plate as represented on the culture plate image. As shown in FIG. 3, the process 230a begins with a step 310 wherein the location of the selection tool is determined. As described above, the selection tool can extend over a range of coordinates, one or more of which can be determined. The location of the selection tool can be determined by the processer running a software application.

After the location of the selection tool is determined, the process 230a moves to a step 320, wherein the location of the edge of the culture plate depicted in the culture plate image is determined. As described above, the location of the edge of the culture plate can be determined by a processer running image processing software that analyzes the features of the culture plate and correlates those features with the image being displayed to the user.

After the location of the edge of the culture plate is determined, the process 230a moves to a step 330, wherein the location determined for the selection tool is compared to the location determined for the culture plate edge.

After the location determined for the selection tool and the location determined for the culture plate edge are compared, the process 230a moves to a decision step 340, wherein a decision is made whether the location of the selection tool is outside of the edge of the culture plate. If the location of the selection tool is outside of the edge of the culture plate, the process 230a moves to a step 350 wherein an error is determined. After an error is determined at step 350, or if the location of the selection tool is not outside of the edge of the culture plate, the process 230a concludes.

As shown in FIG. 4, the process 230b begins with a step 410 wherein the location of the selection tool is determined. As described above, the selection tool can extend over a range of coordinates, one or more of which can be determined. The location of the selection tool can be determined by a processer running a software application.

The process 230b provides an example of analyzing the position of the selection tool to determine if the selection tool is positioned over an internal border of the culture plate as represented on the culture plate image, such as a divider or edge of the culture plate. After the location of the selection tool is determined, the process 230b moves to a step 420, wherein the location of the edge of the culture plate depicted in the culture plate image is determined. As described above, the location of the edge of the culture plate can be determined by a processer running image processing software to calculate this feature of the culture plate and correlate it with the image being displayed.

After the location of the edge of the culture plate is determined, the process 230b moves to a step 430, wherein the location determined for the selection tool is compared to the location determined for the culture plate edge.

After the location determined for the selection tool and the location determined for the culture plate edge are compared, the process 230b moves to a decision step 440, wherein a decision is made whether the location of the selection tool overlays the edge of the culture plate. If the location of the selection tool overlays the edge of the culture plate, the process 230*b* moves to a step 450 wherein an error is determined. After an error is determined at step 450, or if the location of the selection tool does not overlay the edge of the culture plate, the process 230*b* concludes.

The process 230*c* provides an example of analyzing the position of the selection tool to determine if the selection tool is positioned over a previously selected colony location. As shown in FIG. 5, the process 230*c* begins with a step 510 wherein the location of the selection tool is determined. As described above, the selection tool can extend over a range of coordinates, one or more of which can be determined. The location of the selection tool can be determined by a processer running a software application.

After the location of the selection tool is determined, the process 230*c* moves to a step 520, wherein the location of any previously selected colony locations is determined. The location of the previously selected colony locations can be determined by a processer running a software application.

After the location of the previously selected colony locations is determined, the process 230*b* moves to a step 530, wherein the location determined for the selection tool is compared to the location determined for the previously selected colony locations.

After the location determined for the selection tool and the location determined for the previously selected colony locations are compared, the process 230*c* moves to a decision step 540, wherein a decision is made whether the location of the selection tool overlays the previously selected colony locations. If the location of the selection tool overlays the previously selected colony locations, the process 230*c* moves to a step 550 wherein an error is determined. After an error is determined at step 550, or if the location of the selection tool does not overlay previously selected colony locations, the process 230*c* concludes.

Although processes 230*a*, 230*b*, and 230*c* are shown as separate processes, it should be understood that two or more of the processes can be performed in combination or parallel in a process step 230. While specific potential sources of error are addressed in processes 230*a*, 230*b*, and 230*c*, it should be recognized that similar processes can be run for any other potential source of error on a culture plate, for example, by determining the location of the selection tool, determining the location of a potential source of error, comparing the location of the selection tool to the location of the potential source of error, and determining an error if the location of the selection tool overlays the potential source of error. In some embodiments, determining a location of the selection tool include determining geographical coordinates of the selection tool in comparison to geographical coordinates of the culture plate image. Determining the location of a potential source of error can include determining the geographical coordinates of a culture plate feature that may cause a potential error shown on the culture plate image. Comparing the location of the selection tool to the location of the potential source of error can include comparing the geographical coordinates of the selection tool to the geographical coordinates of the culture plate feature shown on the culture plate image. Determining an error can include referencing a table of possible errors related to features of the culture plate. The table of possible errors may be stored in a memory, such as memory 104. The table of possible errors can include, for example, entries for the selection tool overlapping a previously selected colony, the selection tool overlapping a protrusion on the culture plate image such as an edge or divider, and the selection tool being positioned outside of the culture plate shown on the culture plate image.

Figure 6:
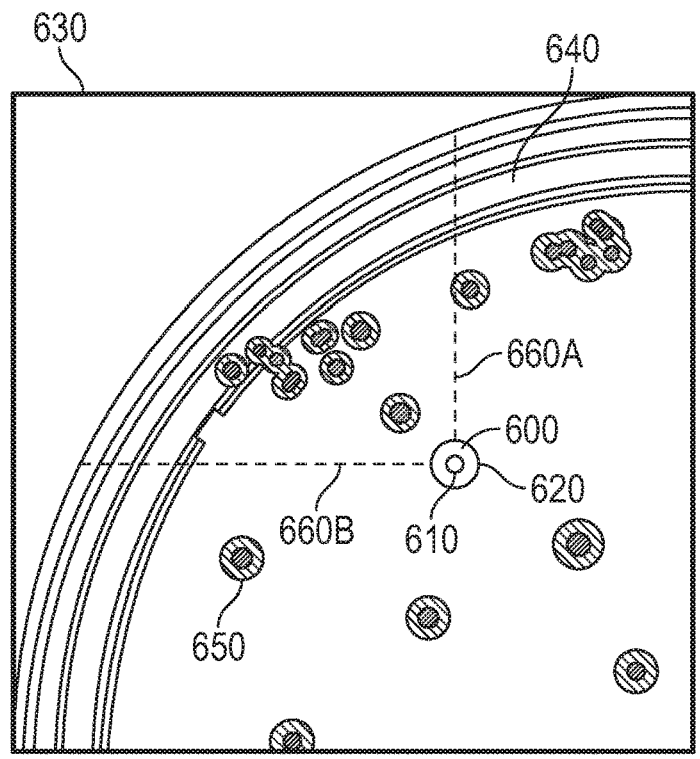
FIG. 6 depicts a selection tool positioned over an image of a culture plate in accordance with an illustrative embodiment of the present invention.

FIGS. 6-9 depict embodiments of selection tools in accordance with the present invention. FIG. 6 depicts an embodiment of a selection tool 600 positioned over an image 630 showing a culture plate 640 having a plurality of colonies, including colony 650. The selection tool 600 includes an inner ring 610 and an outer ring 620. In some embodiments, the inner ring can shaped and sized to substantially match the shape and size of a tip of a pipetting tool, such as picking tool 132. The interior of the inner ring can represent an intended location of pipetting by the picking tool on the culture plate 640.

As described above, the picking tool may be controlled by an automated platform, such as picking instrumentation 130. The picking tool as controlled by the automated platform can have a tolerance of error from the desired location of pipetting. The outer ring 620 can correspond to the tolerance of error of the picking tool from the desired location of pipetting. As described herein, the position of the outer ring 620 can be analyzed to determine if there is a possibility of error such as, for example, striking an obstruction or pipetting the same colony based on two selected colony locations.

The selection tool 600 can further include guidelines 660A and 660B, extending from the selection tool 600 along the y-axis and x-axis, respectively. The guidelines 660A and 660B can provide additional visual aids for positioning of the selection tool 600 on the image 630. The guidelines 660A and 660B may also provide a contrast to the culture plate image in order to improve the visibility of the selection tool on the culture plate image.

Figure 7:
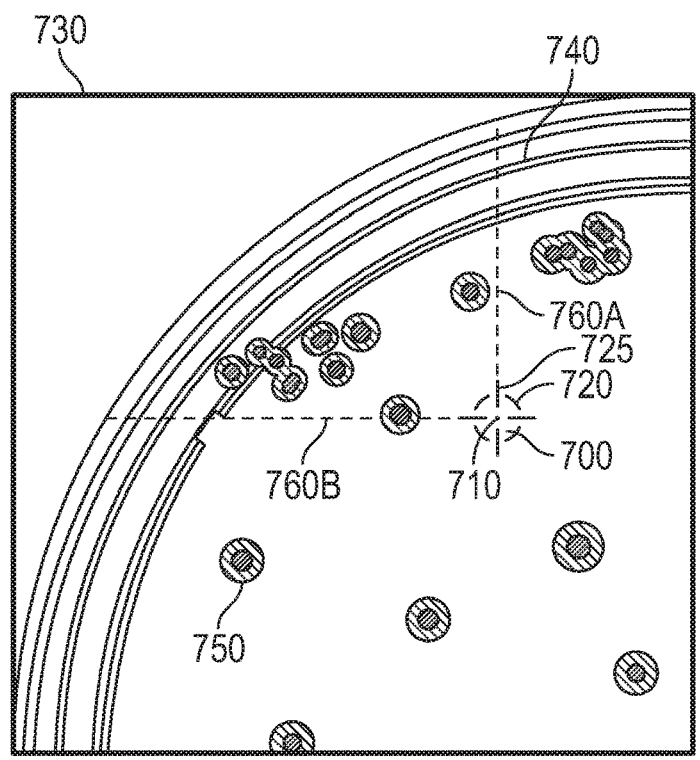
FIG. 7 depicts a selection tool positioned over an image of a culture plate in accordance with an illustrative embodiment of the present invention.

FIG. 7 depicts an embodiment of a selection tool 700 positioned over an image 730 showing a culture plate 740 having a plurality of colonies, including colony 750. The selection tool includes a center dot 710 positioned at a center point of the selection tool 700, a dashed outer ring 720, and a plurality of crosshair lines 725. The center dot 710 can represent an intended location of a center of a picking tool, such as picking tool 132, for pipetting on the culture plate 740.

As described above, the picking tool may be controlled by an automated platform, such as picking instrumentation 130. The picking tool as controlled by the automated platform can have a tolerance of error from the desired location of pipetting. The outer ring 720 can correspond to the tolerance of error of the picking tool from the desired location of pipetting. As described herein, the position of the outer ring 720 can be analyzed to determine if there is a possibility of error such as, for example, striking an obstruction or pipetting the same colony based on two selected colony locations.

The selection tool 700 can include four crosshair lines 725. One pair of crosshair lines 725 can be positioned on the x-axis, each crosshair line being positioned on opposite sides of the center dot 710. A second pair of crosshair lines 725 can be positioned on the y-axis, each crosshair lines being positioned on opposite sides of the center dot 710. The crosshair lines can provide a visual aid for positioning of the selection tool 700. In comparison to the inner ring 610 of FIG. 6, the crosshairs may provide improved visibility to a colony location below the selection tool, The selection tool 700 can further include guidelines 760A and 760B, extending from the selection tool 700 along the y-axis and x-axis, respectively. The guidelines 760A and 760B can provide additional visual aids for positioning of the selection tool 700 on the image 730. The guidelines 760A and 760B may also provide a contrast to the culture plate image in order to improve the visibility of the selection tool on the culture plate image.

Figure 8:
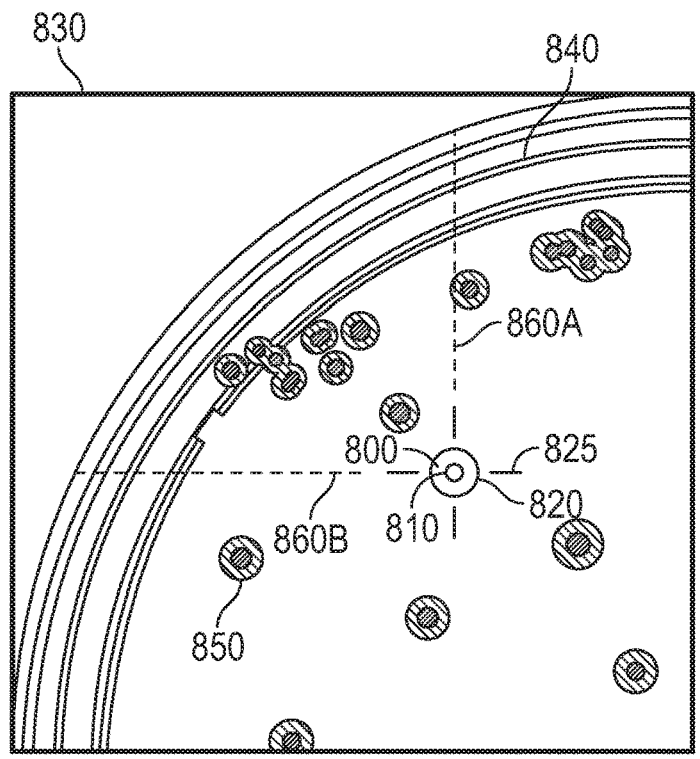
FIG. 8 depicts a selection tool positioned over an image of a culture plate in accordance with an illustrative embodiment of the present invention.

FIG. 8 depicts an embodiment of a selection tool 800 positioned over an image 830 showing a culture plate 840 having a plurality of colonies, including colony 850. The selection tool 800 includes an inner ring 810, an outer ring 820, and a plurality of crosshair lines 825. In some embodiments, the inner ring can shaped and sized to substantially match the shape and size of a tip of a picking tool, such as picking tool 132. The interior of the inner ring can represent an intended location of pipetting by the picking tool on the culture plate 840.

As described above, the picking tool may be controlled by an automated platform, such as picking instrumentation 130. The picking tool as controlled by the automated platform can have a tolerance of error from the desired location of pipetting. The outer ring 820 can correspond to the tolerance of error of the picking tool from the desired location of pipetting. As described herein, the position of the outer ring 820 can be analyzed to determine if there is a possibility of error such as, for example, striking an obstruction or pipetting the same colony based on two selected colony locations.

The selection tool 800 can include four crosshair lines 825. One pair of crosshair lines 825 can be positioned on the x-axis, each crosshair line being positioned on opposite sides of the outer ring 820. A second pair of crosshair lines 825 can be positioned on the y-axis, each crosshair lines being positioned on opposite sides of the outer ring 820. The crosshair lines can provide a visual aid for positioning of the selection tool 800. The selection tool 800 can further include guidelines 860A and 860B, extending from the selection tool 800 along the y-axis and x-axis, respectively. The guidelines 860A and 860B can provide additional visual aids for positioning of the selection tool 800 on the image 830. The guidelines 860A and 860B may also provide a contrast to the culture plate image in order to improve the visibility of the selection tool on the culture plate image.

Figure 9:
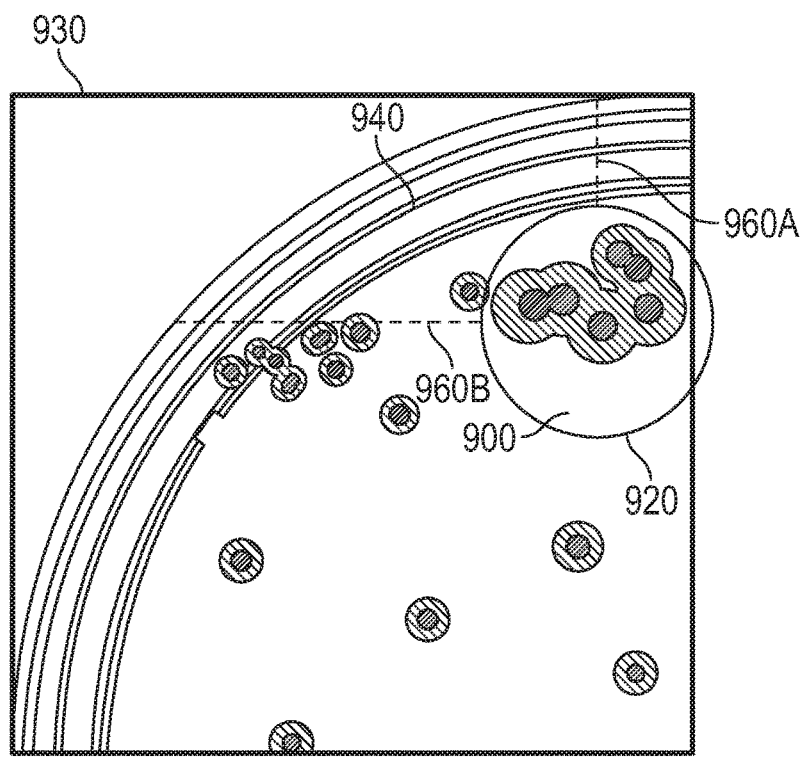
FIG. 9 depicts a selection tool positioned over an image of a culture plate in accordance with an illustrative embodiment of the present invention.

FIG. 9 depicts an embodiment of a selection tool 900 positioned over an image 930 showing a culture plate 940 having a plurality of colonies. The selection tool 900 can include a ring 920. The interior of the ring 920 can show a magnified view of the section of the image 930 below the ring 920. As described above, the picking tool may be controlled by an automated platform, such as picking instrumentation 130. The picking tool as controlled by the automated platform can have a tolerance of error from the desired location of pipetting. The ring 920 can correspond to the tolerance of error of the picking tool from the desired location of pipetting. As described herein, the position of the outer ring 920 can be analyzed to determine if there is a possibility of error such as, for example, striking an obstruction or pipetting the same colony based on two selected colony locations. In some embodiments, the position of the outer ring 920 is itself magnified, such that the position of the outer ring 920 as shown on the image 930 may appear larger than the coordinates for the position of the outer ring 920 that are analyzed to determine a possibility of error.

The selection tool 900 can further include guidelines 960A and 960B, extending from the selection tool 900 along the y-axis and x-axis, respectively. The guidelines 960A and 960B can provide additional visual aids for positioning of the selection tool 900 on the image 930. The guidelines 960A and 960B may also provide a contrast to the culture plate image in order to improve the visibility of the selection tool on the culture plate image.

In some embodiments, a colony selection interface allows a selection between a plurality of different selection tool configurations, such as those shown in FIGS. 6-9. It should be understood that configurations shown for the colony selection tool in FIGS. 6-9 are not limiting. In accordance with the present invention, a colony selection tool can be any size and shape suitable for selecting a colony location and for providing a visual indication of potential sources of error. For example, features from any of the embodiments shown in FIGS. 6-9 can be combined to form a colony selection tool.

Figure 10:
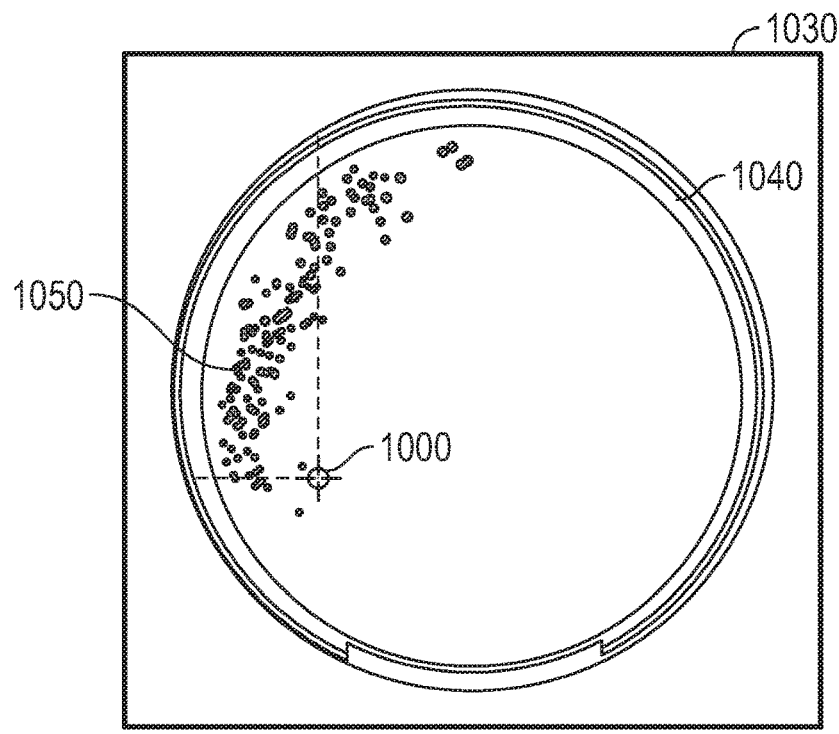
FIG. 10 depicts a selection tool positioned over an image of a culture plate in accordance with an illustrative embodiment of the present invention.
Figure 11:
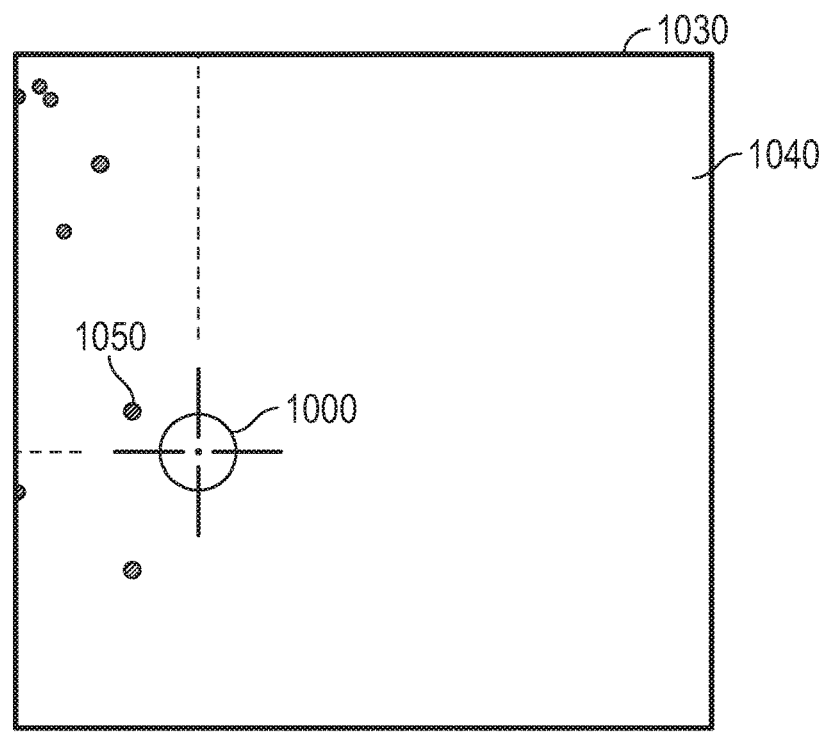
FIG. 11 depicts a selection tool positioned over an image of a culture plate in accordance with an illustrative embodiment of the present invention.

FIG. 10 depicts an illustrative embodiment of a selection tool 1000 positioned over an image 1030 showing a culture plate 1040 having a plurality of colonies 1050. FIG. 11 shows a magnified view of a section of the image 1030 shown in FIG. 10. In an illustrative embodiment, the colony selection interface displaying the image 1030 can allow for manipulation of the image 1030, for example by changing the magnification of the image 1030. As demonstrated by FIGS. 10 and 11, the selection tool 1000 can be configured to change in size to accommodate for the change in magnification of the image 1030. The magnification of the selection tool 1000 can be performed so that the selection tool is indicative of a mechanical tolerance of picking instrumentation, such as picking instrumentation 130, at each degree of magnification.

Figure 12:
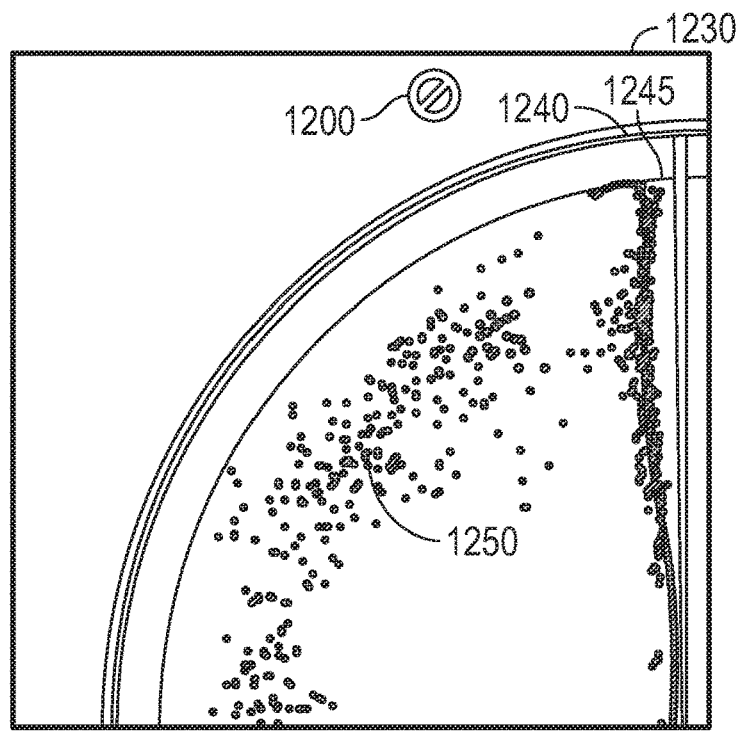
FIG. 12 depicts a selection tool positioned over an image of a culture plate in accordance with an illustrative embodiment of the present invention.

FIG. 12 depicts an illustrative embodiment of a selection tool 1200 positioned over an image 1230 showing a culture plate 1240 having a plurality of colonies 1250. The culture plate 1240 has a culture plate edge 1245. As shown in FIG. 12, the selection tool 1200 is positioned outside of the culture plate edge 1245. FIG. 12 demonstrates an example of error handling, such as that described in step 250 of FIG. 2, when the location of the selection tool is outside of the edge of the culture plate 1245, as described, for example, with respect to step 340 of FIG. 3. As shown in FIG. 12, the selection tool 1200 is shown as a circle with a diagonal line running through it. This shape of the selection tool 1200 indicates that the selection tool is in a location that may result in an error if selected. The shape of the selection tool 1200, as shown in FIG. 12, is configured to be different than the shape of the selection tool 1200 if positioned within the edge 1245 of the culture plate 1200.

Figure 13:
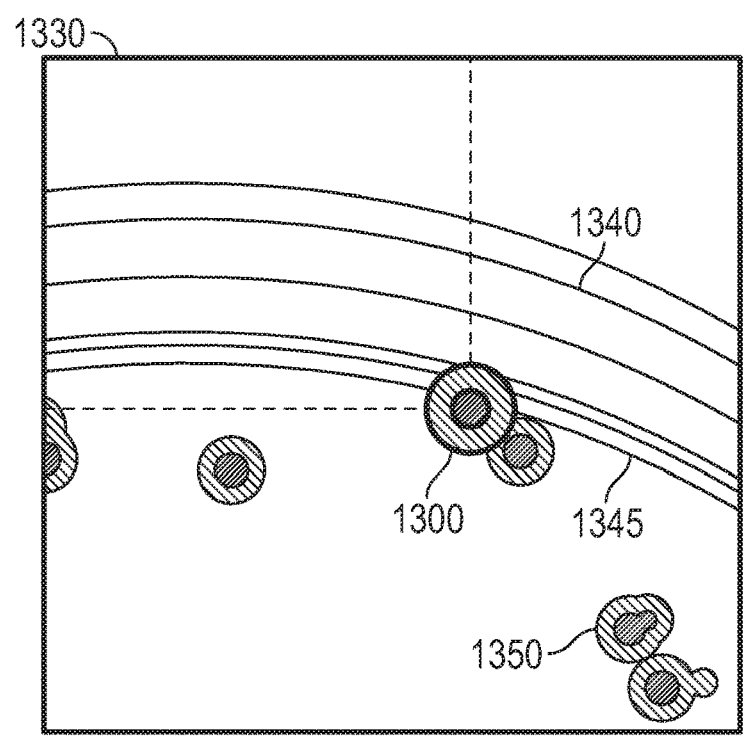
FIG. 13 depicts a selection tool positioned over an image of a culture plate in accordance with an illustrative embodiment of the present invention.
Figure 14:
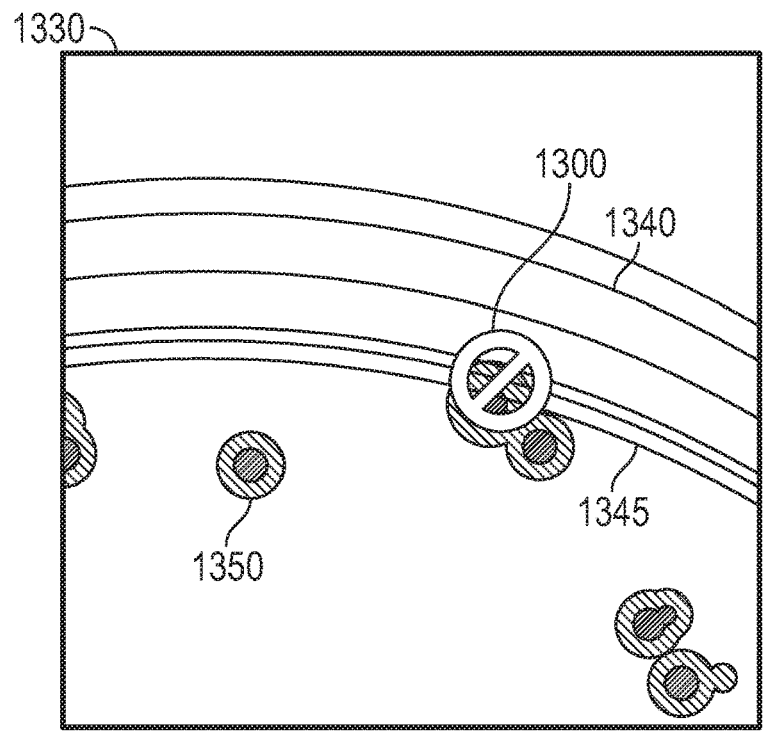
FIG. 14 depicts a selection tool positioned over an image of a culture plate in accordance with an illustrative embodiment of the present invention.

FIG. 13 depicts an illustrative embodiment of a selection tool 1300 positioned over an image 1330 showing a culture plate 1340 having a plurality of colonies, including colony 1350. The culture plate 1340 has a culture plate edge 1345. FIG. 13 shows the selection tool 1300 positioned near an inner wall of the edge 1345. FIG. 14 shows the selection tool 1300 positioned over the image 1330 after the selection tool 1300 has been advanced farther over the edge 1345. As shown in FIG. 14, the shape of the selection tool 1300 has changed in comparison to that shown in FIG. 13. The change in the shape of the selection tool 1300 between FIGS. 13 and 14 demonstrates an example of error handling, such as that described in step 250 of FIG. 2, when the location of the selection tool overlays the edge 1345 of the culture plate 1300, as described, for example, with respect to step 440 of FIG. 4.

Figure 15:
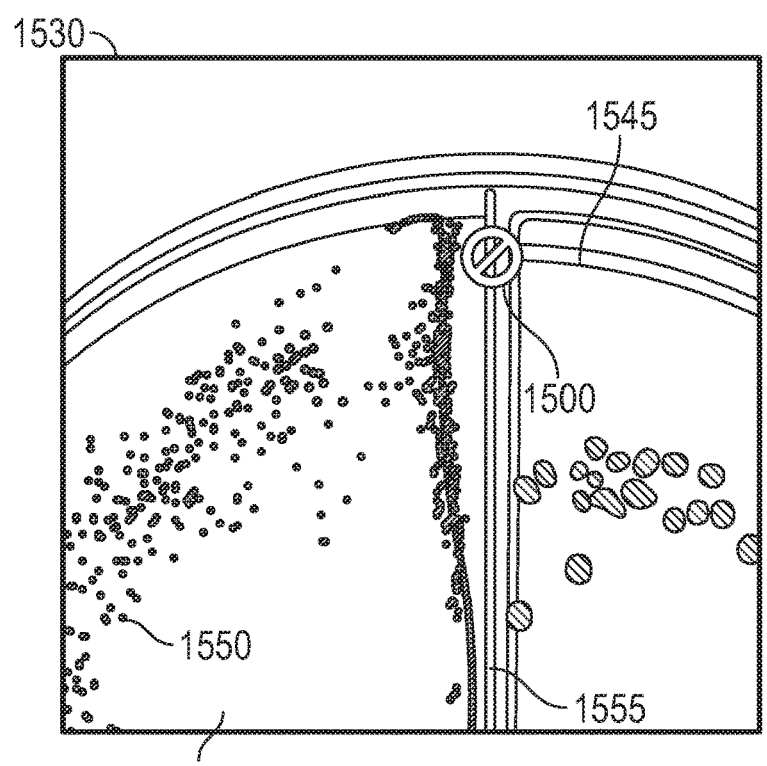
FIG. 15 depicts a selection tool positioned over an image of a culture plate in accordance with an illustrative embodiment of the present invention.

FIG. 15 depicts an illustrative embodiment of a selection tool 1500 positioned over an image 1530 showing a culture plate 1540 having a plurality of colonies, including colony 1550. The culture plate 1540 includes a culture plate edge 1545 and a divider 1555. FIG. 15 demonstrates an example of error handling, such as that described in step 250 of FIG.

2, when the location of the selection tool overlays the position of the divider 1555. The shape of the selection tool 1500 is configured to indicate that the selection tool is in a location that may result in an error if selected.

Figure 16:
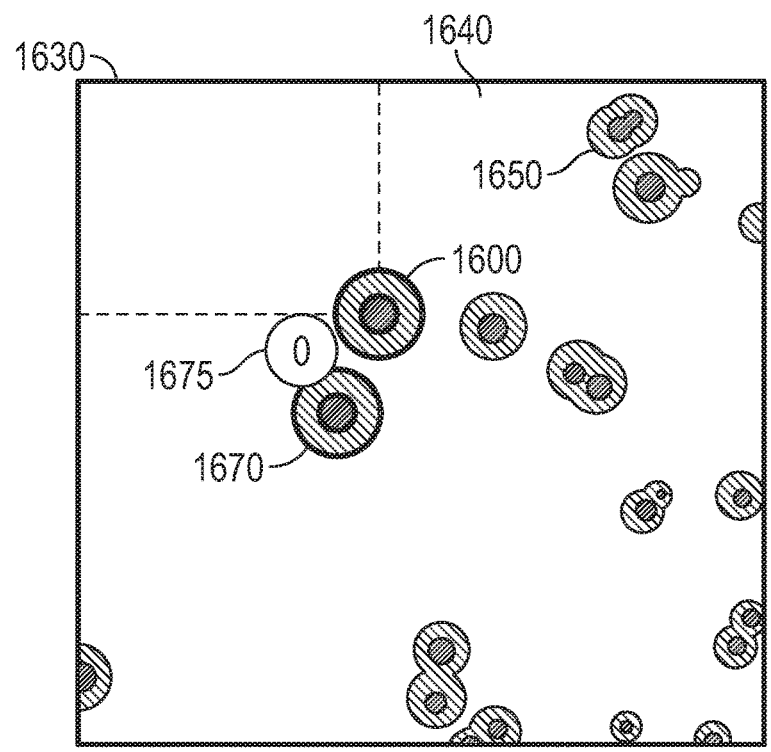
FIG. 16 depicts a selection tool positioned over an image of a culture plate in accordance with an illustrative embodiment of the present invention.

FIG. 16 depicts an illustrative embodiment of a selection tool 1600 positioned over an image 1630 showing a culture plate 1640 having a plurality of colonies, including colony 1650. FIG. 16 also shows a colony marker 1670 and a colony location marker number 1675 associated with the colony location marker 1670. The colony location marker 1670 can be substantially the same shape and size as the selection tool 1600. However, the colony location marker 1670 can be any shape and size sufficient for indicating the position of a colony. For example, the size and shape of the colony location marker 1670 can be similar to the size and shape of any of selection tool 600, selection tool 700, selection tool 800, and selection tool 900, or any combination thereof.

Figure 17:
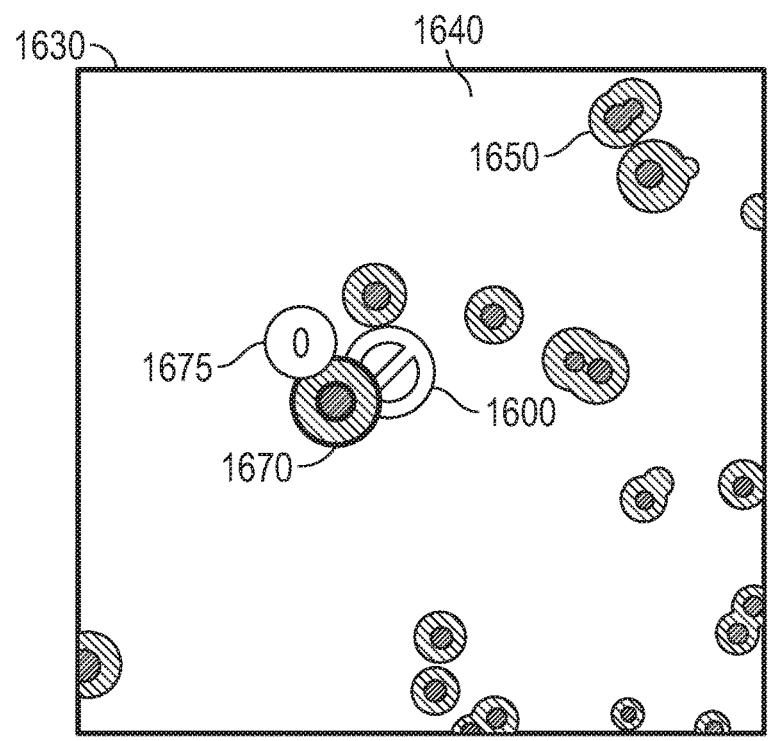
FIG. 17 depicts a selection tool positioned over an image of a culture plate in accordance with an illustrative embodiment of the present invention.

As described herein, colony location marker 1670 can represent a desired location that has been selected for pipetting by a picking tool, such as picking tool 132. The colony location marker 1670 can be sized and shaped to accommodate a tolerance of the picking tool. As described herein the selection tool 1600 is also sized and shaped to accommodate a tolerance of the picking tool. In FIG. 16, the selection tool 1600 is positioned apart from the marker 1670. FIG. 17 shows the selection tool 1600 positioned over the image 1630. In FIG. 17, the selection tool 1600 is positioned such that the outer edge of the selection tool 1600 overlays a section of the marker 1670. As shown in FIG. 17, the shape of the selection tool 1600 has changed in comparison to that shown in FIG. 16. The change in the shape of the selection tool 1600 between FIGS. 16 and 17 demonstrates an example of error handling, such as that described in step 250 of FIG. 2, when the location of the selection tool overlays a previously selection colony location, as described, for example, with respect to step 540 of FIG. 5.

Implementations disclosed herein provide systems, methods and apparatus for a selecting a colony location. One skilled in the art will recognize that these embodiments may be implemented in hardware, software, firmware, or any combination thereof.

The functions described herein may be stored as one or more instructions on a processor-readable or computer-readable medium. The term "computer-readable medium" refers to any available medium that can be accessed by a computer or processor. By way of example, and not limitation, such a medium may comprise RAM, ROM, EEPROM, flash memory, CD-ROM or other optical disk storage, magnetic disk storage or other magnetic storage devices, or any other medium that can be used to store desired program code in the form of instructions or data structures and that can be accessed by a computer. Disk and disc, as used herein, includes compact disc (CD), laser disc, optical disc, digital versatile disc (DVD), floppy disk and Blu-ray® disc where disks usually reproduce data magnetically, while discs reproduce data optically with lasers. It should be noted that a computer-readable medium may be tangible and non-transitory. The term "computer-program product" refers to a computing device or processor in combination with code or instructions (e.g., a "program") that may be executed, processed or computed by the computing device or processor. As used herein, the term "code" may refer to software, instructions, code or data that is/are executable by a computing device or processor.

Software or instructions may also be transmitted over a transmission medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of transmission medium.

The methods disclosed herein comprise one or more steps or actions for achieving the described method. The method steps and/or actions may be interchanged with one another without departing from the scope of the claims. In other words, unless a specific order of steps or actions is required for proper operation of the method that is being described, the order and/or use of specific steps and/or actions may be modified without departing from the scope of the claims.

It should be noted that the terms "couple," "coupling," "coupled" or other variations of the word couple as used herein may indicate either an indirect connection or a direct connection. For example, if a first component is "coupled" to a second component, the first component may be either indirectly connected to the second component or directly connected to the second component. As used herein, the term "plurality" denotes two or more. For example, a plurality of components indicates two or more components.

The term "determining" encompasses a wide variety of actions and, therefore, "determining" can include calculating, computing, processing, deriving, investigating, looking up (e.g., looking up in a table, a database or another data structure), ascertaining and the like. Also, "determining" can include receiving (e.g., receiving information), accessing (e.g., accessing data in a memory) and the like. Also, "determining" can include resolving, selecting, choosing, establishing and the like.

The phrase "based on" does not mean "based only on," unless expressly specified otherwise. In other words, the phrase "based on" describes both "based only on" and "based at least on."

In the foregoing description, specific details are given to provide a thorough understanding of the examples. However, it will be understood by one of ordinary skill in the art that the examples may be practiced without these specific details. For example, electrical components/devices may be shown in block diagrams in order not to obscure the examples in unnecessary detail. In other instances, such components, other structures and techniques may be shown in detail to further explain the examples.

Headings are included herein for reference and to aid in locating various sections. These headings are not intended to limit the scope of the concepts described with respect thereto. Such concepts may have applicability throughout the entire specification.

It is also noted that the examples may be described as a process, which is depicted as a flowchart, a flow diagram, a finite state diagram, a structure diagram, or a block diagram. Although a flowchart may describe the operations as a sequential process, many of the operations can be performed in parallel, or concurrently, and the process can be repeated. In addition, the order of the operations may be re-arranged. A process is terminated when its operations are completed. A process may correspond to a method, a function, a procedure, a subroutine, a subprogram, etc. When a process corresponds to a software function, its termination corresponds to a return of the function to the calling function or the main function.

The previous description of the disclosed implementations is provided to enable any person skilled in the art to make or use the present invention. Various modifications to these implementations will be readily apparent to those skilled in the art, and the generic principles defined herein may be applied to other implementations without departing from the spirit or scope of the invention. Thus, the present invention is not intended to be limited to the implementations shown herein but is to be accorded the widest scope consistent with the principles and novel features disclosed herein.

What is claimed is:

1. A system for selecting colony locations on a culture plate image, comprising:
    a computer system comprising: a user interface configured to display a culture plate image and a selection tool; and
    a processor configured to:
        determine a location of the selection tool on the culture plate image, the selection tool comprising a cursor configured to move across a display screen displaying the culture plate image and configured to facilitate selection of one or more colony locations;
        determine a location of a potential source of error on the culture plate image;
        compare the location of the selection tool to the location of the potential source of error; and
        determine an error when the location of the selection tool overlays the location of the potential source of error.

2. The system of claim 1, further comprising an incubation system comprising:
    an incubator housing at least one culture plate having a plurality of microorganisms; and
    an imaging device configured to capture an image of the at least one culture plate.

3. The system of claim 1, wherein the potential source of error comprises an edge of a culture plate shown in the culture plate image.

4. The system of claim 1, further comprising an input configured to control the location of the selection tool on the culture plate image.

5. The system of claim 1, further comprising a picking instrumentation comprising an automated picking tool configured to remove one or more colony samples from a culture plate.

6. The system of claim 1, wherein the selection tool is shaped and sized to correlate to a mechanical tolerance of an automated picking tool.

7. The system of claim 1, wherein the processor is configured to receive a selection of at least one colony location via the selection tool.

8. The system of claim 7, wherein the processor is configured to add a visual indicator to the culture plate image marking the at least one colony location selection.

9. The system of claim 8, wherein the visual indicator is shaped and sized to correlate to a mechanical tolerance of an automated picking tool.

10. The system of claim 7, further comprising an automated picking tool, wherein the automated picking tool is configured to pick a colony of microorganisms corresponding to the at least one colony location selection.

11. The system of claim 1, wherein the user interface is configured to display a plurality of culture plate images simultaneously.

12. The system of claim 1, wherein the processor is configured to determine a location of the selection tool on the culture plate image by determining the geographical coordinates of the selection tool as compared to the geographical coordinates of the culture plate image.

13. The system of claim 1, wherein the processor is configured to compare the location of the selection tool to the location of the potential source of error by matching the geographical coordinates of the selection tool on the user interface to the geographical coordinates of a culture plate feature shown in the culture plate image.

14. The system of claim 1, wherein the processor is configured to determine an error by referencing a table of possible errors relating to one or more features of a culture plate.

15. A method for selecting colony locations on a culture plate image, comprising:
    determining, by a processor, a location of a selection tool on the culture plate image, the selection tool comprising a cursor configured to move across a display screen displaying the culture plate image and configured to facilitate selection of one or more colony locations;
    determining, by the processor, a location of a potential source of error on the culture plate image;
    comparing, by the processor, the location of the selection tool to the location of the potential source of error; and
    determining, by the processor, an error when the location of the selection tool overlays the location of the potential source of error.

16. The method of claim 15, wherein the selection tool is shaped and sized to correlate to a mechanical tolerance of an automated picking tool.

17. The method of claim 15, wherein the potential source of error comprises an edge of a culture plate shown in the culture plate image.

18. The method of claim 15, further comprising receiving, by the processor, at least one colony location selection using the selection tool.

19. The method of claim 18, further comprising adding, by the processor, a visual indicator to the culture plate image marking the at least one colony location selection.

20. The method of claim 19, wherein the visual indicator is shaped and sized to correlate to a mechanical tolerance of an automated picking tool.

21. The method of claim 15, wherein the potential source of error comprises a previously selected colony location.

22. The method of claim 15, further comprising initiating, by the processor, a colony selection interface, wherein initiating the colony selection interface comprises generating the selection tool.

23. The method of claim 18, further comprising pipetting a colony of microorganisms corresponding to the at least one colony location selection.

24. The method of claim 15, further comprising imaging a culture plate housing a plurality of microorganisms.

25. The method of claim 15, wherein determining, by the processor, the location of the selection tool on the culture plate image comprises determining the geographical coordinates of the selection tool as compared to the geographical coordinates of the culture plate image.

26. The method of claim 15, wherein comparing, by the processor, the location of the selection tool to the location of the potential source of error comprises matching the geographical coordinates of the selection tool on the user interface to the geographical coordinates of a culture plate feature shown in the culture plate image.

27. The method of claim 15, wherein determining, by the processor, the location of the potential source of error on the culture plate image comprises referencing a table of possible errors relating to one or more features of a culture plate.

* * * * *